(12) United States Patent
Wilson et al.

(10) Patent No.: US 9,265,414 B2
(45) Date of Patent: Feb. 23, 2016

(54) METHODS AND SYSTEMS FOR MEASURING INTERPUPILLARY DISTANCE

(71) Applicants: Hal Edward Wilson, Raleigh, NC (US); James Gerard Welch, Raleigh, NC (US)

(72) Inventors: Hal Edward Wilson, Raleigh, NC (US); James Gerard Welch, Raleigh, NC (US)

( * ) Notice: Subject to any disclaimer, the term of this patent is extended or adjusted under 35 U.S.C. 154(b) by 88 days.

(21) Appl. No.: 14/246,763

(22) Filed: Apr. 7, 2014

(65) Prior Publication Data
US 2014/0218680 A1   Aug. 7, 2014

Related U.S. Application Data

(63) Continuation of application No. 13/914,586, filed on Jun. 10, 2013, now Pat. No. 8,690,326, which is a continuation of application No. 13/094,349, filed on Apr. 26, 2011, now Pat. No. 8,459,792.

(60) Provisional application No. 61/343,137, filed on Apr. 26, 2010.

(51) Int. Cl.
*A61B 3/10* (2006.01)
*A61B 3/11* (2006.01)
*G02C 13/00* (2006.01)
*G06T 7/60* (2006.01)

(52) U.S. Cl.
CPC . *A61B 3/11* (2013.01); *A61B 3/111* (2013.01); *G02C 13/005* (2013.01); *G06T 7/60* (2013.01); *G06T 2207/30041* (2013.01); *G06T 2207/30204* (2013.01)

(58) Field of Classification Search
CPC .......................................................... A61B 3/113
USPC .......................................... 351/204, 246, 200
See application file for complete search history.

(56) References Cited

U.S. PATENT DOCUMENTS 6,142,628 A * 11/2000 Saigo ............................ 351/204

* cited by examiner

*Primary Examiner* — Hung Dang
(74) *Attorney, Agent, or Firm* — James M. Smedley LLC; James Michael Smedley, Esq.

(57) ABSTRACT

The proposed innovation provides methods and systems for measuring the interpupillary distance. The proposed innovation provides a fitting pad (102) having two detection points (104 and 106). The fitting pad is placed on the forehead of the user and an image is captured. The image is uploaded and pupil distance calculator software locates the fitting detection points and calculates the distance in pixels of the left and right X, Y coordinates. The software creates an image scale by dividing the pixel counts between the detection points. The software automatically locates the X, Y coordinates between the center of the left and right pupils and calculates the distance in pixels. The resulting pixel distance divided by the image scale provides the interpupillary distance in millimeter. In embodiments, segment height is calculated based upon an image imported by the user and the combined scaled images of the user and the frame.

20 Claims, 4 Drawing Sheets

```
Exemplary Fitting Pad Measurement Calculations

EYES
       Left    Right
  x     361     469          11,664.00
  y     264     258              36.00
                             11,700.00
                                108.17
                        PD =       53.524

FITTING PAD
       Left    Right
  x     359     460          10,201.00
  y     195     192               9.00
                             10,210.00
                                101.04
                   Pixels per MM    2.021

SIZE of
                                    50.000    MM
                   Fitting Pad ▓▓▓ = Input Values
```

METHODS AND SYSTEMS FOR MEASURING INTERPUPILLARY DISTANCE

CROSS-REFERENCE TO RELATED APPLICATIONS

This application is a continuation in part of non-provisional patent application, U.S. patent application Ser. No. 13/914,586 filed on Jun. 10, 2013, which is hereby incorporated by reference in its entirety.

FIELD OF THE INNOVATION

The present innovation relates to a methods and systems for measuring interpupillary distance. More specifically, the innovation relates to a computer aided methods and systems for measuring interpupillary distance with minimal manual interference.

BACKGROUND OF THE INNOVATION

Interpupillary Distance (IPD) is the distance between the centers of the pupils in each eye. This measurement is used when preparing to make prescription eyeglasses. Positioning lenses correctly in relation to the centre of the pupils is especially important for higher powered lenses due to the location of the optical centre of the lenses.

However, it is very difficult to manually take this measurement against two moving objects (left and right eye) and almost impossible to measure one's own pupillary distance.

As examples of known art, I refer to U.S. Pat. No. 7,322,697 wherein there is disclosed a method of measuring a pupil distance. The method includes locating an imaging device at a position a predetermined distance away from a member attached to eyeglasses worn by a subject. The member has two indicators. The method further includes photographing the subject while the subject observes an observing point in the vicinity of the imaging device, measuring an apparent distance between left and right pupils of the subject on a photographed image, and obtaining an interpupillary distance PD m accordance with: PD=[(A+B).times.C·times.E]/(A.times.D) (1) where "A" represents a distance between the member and the imaging device, "B" represents a distance between a center of rotation of each eye of the subject and the member, "C" represents an actual distance between the indicators in a direction parallel with a line connecting left and right centers of rotation of the subject, "D" represents an apparent distance between the indicators in the direction parallel with the line connecting the left and right centers of rotation on the photographed image, and "E" represents the apparent distance between the left and right pupils of the subject on the photographed image.

Again m U.S. Pat. No. 5,822,032, a device for measuring the interpupillary distance between the pupils of the eyes of that person is disclosed. The device includes a frame having a face and a first hole extending through the frame from the face which is positional at one of the person's two pupils. A disk is mounted juxtaposed to the frame which is rotatable about an axis perpendicular to the frame's face. The disk has a surface and a plurality of second holes extending through the disk from its surface. By rotating the disk, one of the second holes is positional at the other of the person's pupils. The interpupillary distance (IPD) is equal or approximately equal to the distance between the centers of the first and second holes when the holes are positioned at the person's respective pupils.

Again in U.S. Pat. No. 6,535,223, a method for determining the real-world interpupillary distance is provided. The method includes determining the interpupillary distance for a user from an image provided for use with "virtual try-on" technology. This is accomplished by having the user place a reference object on or near their face in the virtual try-on image. The reference object should be one that is a standard size and is readily available to users. Alternatively, the reference object used can be the iris in a user's own eye, since it is well known that the human iris is of a relatively fixed size from individual to individual. When using a reference object, the user takes the facial picture with the reference object on generally the same plane and distance from the camera as their face, such as by holding a quarter on their chin with a single finger. The image is then submitted to the web site as is now standard with sites utilizing virtual try-on technology. After the image is transmitted, the image can then be resized and used to try-on different frames as is known in the prior art. Alternatively, a second image without a reference object can be used for trying on frames. Once the frames are selected and an order for the frames placed, the image with the reference object is associated with the order. The width of the reference object on the image is then compared to the measured interpupillary distance on the image. These measurements can be made in pixels as opposed to real-world distances, because the image is being provided in a pixilated digital file. The actual interpupillary distance can then be calculated by comparing the ratio of the distances measured in the image with the known width of the reference object. Similarly, the virtual interpupillary distance or segment height (usually called "seg height") needed for multi-focal elements can be determined by measuring the height using the frame on face virtual try-on technology. The measured distance on the image is converted to a real world measurement using the ratio obtained from the reference image.

All of these stated methods and devices/systems and some other methods and devices/systems presently known in the art have had some flaws in design or mechanism and lacks precision. Most of the existing devices are too expensive to be practical for most users. Some shortfalls of the existing methods and systems include manual interference, leading to inaccuracy in measurements. In light of this, there is a need for a method and system that overcomes these constraints.

SUMMARY

The present innovation is directed to methods and systems for measuring the interpupillary distance. The proposed innovation provides a fitting pad having two detection points. The fitting pad is placed on the forehead of the user and an image is captured. The captured image is uploaded and pupil distance calculator software automatically locates the fitting detection points and calculates the distance in pixels of the left and right X, Y coordinates. The said software creates an image scale by dividing the pixel counts between the detection points. The said software automatically locates the X, Y coordinates between the center of the left and right pupils and calculates the distance in pixels. The resulting pixel distance divided by the image scale provides the interpupillary distance in millimeter.

In embodiments, the distance between the detection points is at least 40 mm. In embodiments, the detection points are printed on a specialized fitting frame or a custom trial frame and the detection points are located at a consistent, fixed distance.

In embodiments, the detection points are printed in such a manner so that there is a high level of contrast between the detection points and the fitting pad surface.

In embodiments, the detection points are located by the difference in level of contrast. In embodiments, the detection points are located by their respective shape and size.

In embodiments, the centres of the left and right eye pupil are located by an attribute associated with the image of the eye. In embodiments, the fitting pad is provided in a pre-printed format or can be printed by a user on a personal computer.

In embodiments, the fitting pad can be of different sizes. In embodiments, the size of the fitting pad is based on the age of the user or some other similar attributes of the user.

In addition to the interpupillary distance, other measurements such as segment height are calculated which are required while manufacturing multi-focal lenses.

According to an embodiment of the present invention, a method for measuring interpupillary distance, the method comprising the steps of: producing three dimensional spatial depth data from a range imaging sensor of a range imaging depth camera device to a person within a field of view of the range imaging sensor; capturing two dimensional color data of the object with a color imaging sensor of the range imaging depth camera device; uploading said three dimensional spatial data and said two dimensional color data to a computing device; mapping X, Y coordinates of the three dimensional spatial depth data with X, Y coordinates of the two dimensional color data through use of device specific mapping relationships between the range imaging depth sensor and the color imaging sensor; and utilizing the range imaging sensor to automatically locate X, Y, and Z coordinate positions of the left and right pupils of the person where the X and Y coordinate positions are centered on the pupil and the Z coordinate position is a distance from a plane located at the range imaging sensor to the surface of the left and right pupil.

According to an embodiment of the present invention, the method further comprises the step of displaying said two dimensional color data in the form of an image on a display communicatively connected to said computing device.

According to an embodiment of the present invention, the computing device is further configured to provide indicators on the display that show estimated location points for the pupils of the person.

According to an embodiment of the present invention, the computing device prompts the person to move the estimated location points for the pupils of the person.

According to an embodiment of the present invention, the computing device is configured with a touch screen display.

According to an embodiment of the present invention, the computing device receives signals relating to where the person touches the touchscreen and determines confirmation of the person with respect to the location of the pupils of the person in said two dimensional color data.

According to an embodiment of the present invention, the method further comprises the step of presenting a virtual image of the person wearing a pair of glasses, wherein the glasses are sized in conjunction with said X, Y, and Z coordinate positions of the left and right pupils of the person.

According to an embodiment of the present invention, a method for measuring interpupillary distance, the method comprising the steps of: producing three dimensional spatial depth data from a range imaging sensor of a range imaging depth camera device to a person within a field of view of the range imaging sensor; capturing two dimensional color data of the object with a color imaging sensor of the range imaging depth camera device; uploading said three dimensional spatial data and said two dimensional color data to a computing device; mapping X, Y coordinates of the three dimensional spatial depth data with X, Y coordinates of the two dimensional color data through use of device specific mapping relationships between the range imaging depth sensor and the color imaging sensor; and identifying X and Y pixel coordinate positions of a left and right pupil in the two dimensional color data, developing a pre-defined extrinsic linear relationship that defines image scale as a function of depth from the color imaging sensor to the person by using constant intrinsic parameters of the color imaging sensor; computing image scale using the extrinsic linear relationship and the averaged measured depth data (Z coordinate) to the left and right pupils; calculating a distance between centers of the left and right pupils using the image scale and number of pixels between the centers of the left and right pupil.

According to an embodiment of the present invention, a range imaging depth system comprises: a range imaging sensor for producing three dimensional spatial depth data; a color imaging sensor for capturing two dimensional color data; and a pupil distance calculator unit for incorporating device specific relationship information between the three dimensional spatial depth data and the two dimensional color data to map X,Y coordinates of the three dimensional spatial depth data with X, Y coordinates of the two dimensional color data.

According to an embodiment of the present invention, the system further includes a display communicatively connected to said pupil distance calculator unit, said display configured to display said two dimensional color data in the form of an image.

According to an embodiment of the present invention, the display provides indicators that show estimated location points for the pupils of the person.

According to an embodiment of the present invention, said pupil distance calculator unit prompts the person, via the display, to move the estimated location points for the pupils of the person.

According to an embodiment of the present invention, the system further includes a touch screen display.

According to an embodiment of the present invention, the pupil distance calculator unit is configured to receive signals relating to where the person touches the touch screen display and determines confirmation of the person with respect to the location of the pupils of the person in said two dimensional color data.

BRIEF DESCRIPTION OF FIGURES

The systems and methods described herein may be understood by reference to the following figures:

FIG. 3 depicts a table showing exemplary calculations for measuring the interpupillary distance in accordance with various embodiments of the present innovation.

While the above-identified figures set forth preferred embodiments of the innovation, other embodiments are also contemplated, as noted in the discussion. In all cases, this disclosure presents the present innovation by way of representation and not limitation. It should be understood that numerous other modifications and embodiments can be devised by those skilled in the art which fall within the scope and spirit of the principles of this innovation.

DETAILED DESCRIPTION OF FIGURES

Figure 1:
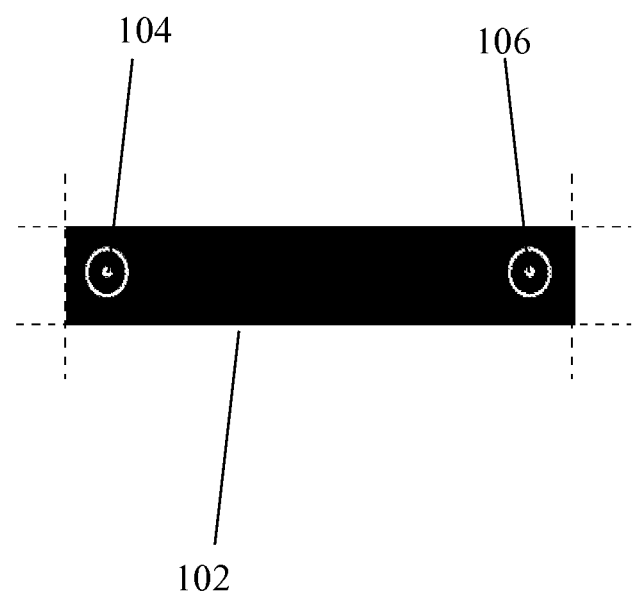
FIG. 1 illustrates a fitting pad in accordance with various embodiments of the present innovation.

Referring now to the drawings where the showings are for the purpose of describing the preferred embodiment of the proposed innovation and not for limiting the same, FIG. 1 illustrates a fitting pad 102. The fitting pad 102 along with the other system elements and method steps enables the accurate measurement of the interpupillary distance.

In an embodiment of the present innovation, the fitting pad 102 can be provided in a pre-printed format or printed by a user on a personal computer, laptop, and the like. In an embodiment of the present innovation, the fitting pad 102 can be of different sizes. Fitting pad 102 of different sizes can be made based on the age of the user or some other similar attributes of the user.

The fitting pad 102 has two detection points 104 and 106. The detection points 104 and 106 are on the ends of the fitting pad 102 and are designed to reduce errors in determining the exact end points. In an embodiment of the present innovation, the distance between the detection points 104 and 106 is at least 30 mm. In an embodiment of the present innovation, the fitting pad detection points 104 and 106 can also be printed on a specialized fitting frame or a custom trial frame where the detection points 104 and 106 are located at a consistent, fixed distance. The detection points 104 and 106 are printed in such a manner so that there is a high level of contrast between the detection points 104 and 106 and the fitting pad 102 surfaces.

Figure 2:
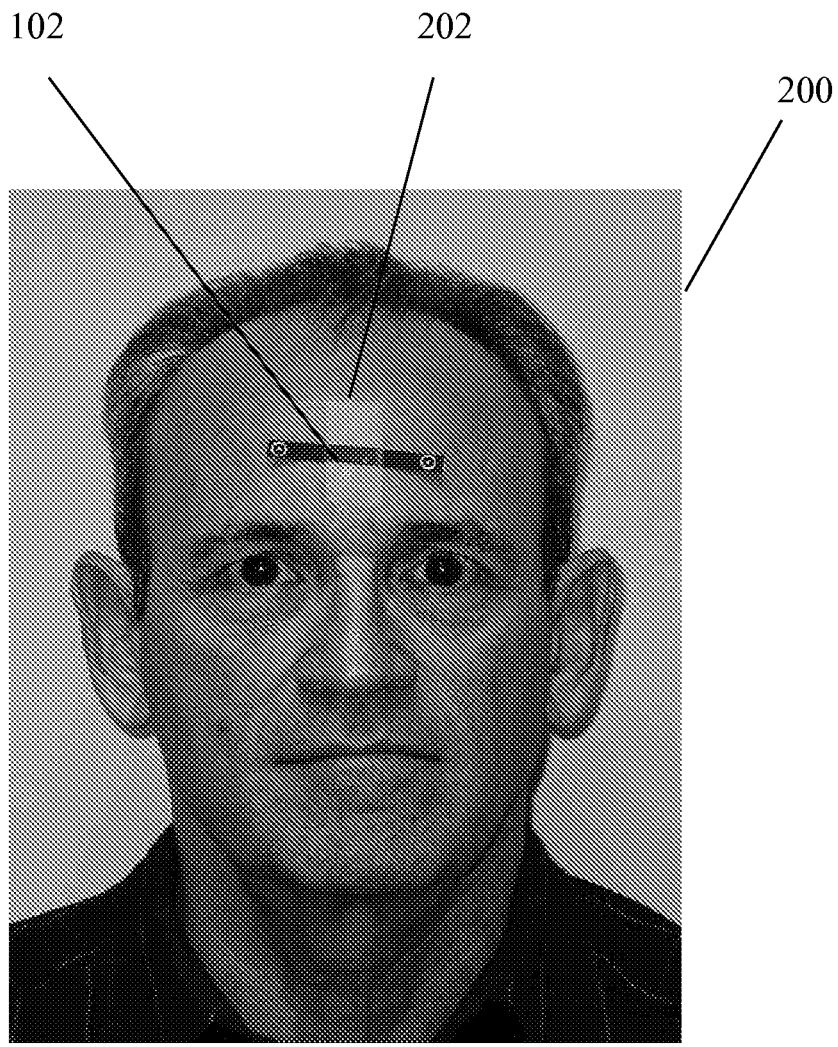
FIG. 2 depicts the fitting pad being placed on the forehead of the user in accordance with various embodiments of the present innovation.

Referring to FIG. 2, the fitting pad 102 is placed on the forehead of the user. In an embodiment of the present innovation, a tape 202 may be attached on the center to make the fitting pad stick to the forehead of the user. In an embodiment of the present innovation, a photo 200 focusing the eyes of the user and his forehead having the fitting pad 102 is captured. A known person in the vicinity of the user can capture the photo 200.

In an embodiment of the present innovation, pupil distance calculator software imports the photo 200. The photo distance calculator software 200 automatically locates the fitting detection points 104 and 106 of the fitting pad 102. As there is a high level of contrast between the detection points 104 and 106 and the fitting pad 102 surface, the pupil distance calculator identify these detection points based on the level of contrast. In another embodiment of the present invention, the pupil distance calculator software may also use the shape or geometry of the detection points 104 and 106 in addition or in conjunction with the contrast element. It may be noted that pupil distance calculator software of the proposed innovation is explained to locate the detection points 104 and 106 on the fitting pad 102 by using the difference in the level of contrast, the shape or geometry of the detection points 104 and 106; however, those skilled in the art would appreciate that the detection points 104 and 106 can be located by any technology presently known in the art.

On identifying the detection points 104 and 106, the pupil distance calculator software calculates the distance between the detection point 104 and 106 in pixels by tracking their respective X, Y coordinates. In an exemplary scenario, the X, Y coordinate of the detection point 104 can be 359 and 195 respectively. The X, Y coordinates of the detection point 106 can be 460 and 192 respectively. So, the distance in pixels between the two detection points will be 101.04. In an embodiment of the present invention, to determine the number of pixels between the two detection points on the fitting pad 102 when the detection points 104 and 106 are not perfectly horizontal; calculations are performed using Pythagorean Theorem. For a right triangle, the square of the hypotenuse is equal to the sum of the squares of the other two sides. Thus, for two points in a pixilated digital image, with each point having an x and y coordinate, the number of pixels between the selected points will be square root of the difference of the x coordinates squared plus the difference of the y coordinates squared.

In an embodiment of the present innovation, the pupil distance calculator software creates an image scale. In this embodiment of the present innovation, the image scale is created by dividing the above calculated pixel counts between the detection points 104 and 106 with the already known distance of the detection points 104 and 106 (say 50 mm in this case). In the above stated scenario, the image scale will be 2.021 pixels per mm (101.04/50).

In an embodiment of the present innovation, the pupil distance calculator software also automatically locates the X, Y coordinates between the center of the left and right pupils. The pupil distance calculator software locates the X; Y coordinates of the center of the left and right pupil based on the identification of the size of eye, level of contrast, and the like. It may be noted that pupil distance calculator software of the proposed innovation is explained to center of the left and right pupil by using the difference in the level of contrast, shape and size of the eye, and the like; however, those skilled in the art would appreciate that the center of the left and right pupil can be located by any technology presently known in the art.

Once the centers of the left and right pupil are located, the distance between them in pixels is calculated. In the above stated example, the X, Y coordinate of the user's left eye is 361 and 264 respectively and the X, Y coordinate of the user's right eye is 469 and 258 respectively. So, the distance in pixels between the centers of the left and right pupil is 108.17.

In an embodiment of the present innovation, the resulting pixel distance divided by the image scale is the pupillary distance in mm. In the above stated example, the pupillary distance will be 53.524 (108.17/2.021). This pupillary distance of the user can be used to fit eyeglasses. In an embodiment of the present invention, to determine the number of pixels between the two detection points on the fitting pad 102 and the distance between the pupils when the detection points 104 and 106 are not perfectly horizontal, calculations are performed using Pythagorean theorem. For a right triangle, the square of the hypotenuse is equal to the sum of the squares of the other two sides. Thus, for two points in a pixilated digital image, with each point having an x and y coordinate, the number of pixels between the selected points will be square root of the difference of the x coordinates squared plus the difference of the y coordinates squared.

It may be noted that a table 300 showing the calculations in the above stated example has been shown in the FIG. 3. Note that the calculations shown in the above stated example is just for explaining the innovation in a simplistic manner and should not be taken in a limiting sense.

In another embodiment of the present invention, a method for measuring the interpupillary distance is provided through the use of a range imaging depth camera. In general, range imaging depth cameras include a range imaging sensor that produces 3D spatial depth data from the range imaging sensor to an object within the sensor field of view. Range imaging depth cameras also generally include a color imaging sensor that captures 2D color data of the object within the color imaging sensor field of view. Through use of the range imaging depth camera, a person, whose interpupillary distance is to be computed, is positioned in the field of view and situated facing the range imaging depth camera.

At this point, the range imaging depth camera captures and uploads 3D spatial depth data of the person and the range imaging depth camera further captures and uploads the 2D color Image data (e.g. RGB Image) of the person. Now that the image data has been provided to the system, it is communicated to the pupil distance calculator software where processing of the interpupillary distance occurs.

The pupil distance calculator software is configured for incorporating the range imaging depth camera device specific relationship between the 3D spatial depth data and the 2D color data to map the X,Y coordinates of the 3D spatial depth data with the X, Y coordinates of the 2D color image. The pupil distance calculator software is configured to utilize the range imaging depth sensor data to automatically locate the X,Y, and Z (spatial depth data) coordinate positions of the left and right pupils whereas the X and Y coordinates are centered on the pupil and the Z coordinate is the distance from the plane located at the range imaging sensor to the surface of the pupil. Alternatively, the pupil distance calculator software can be configured to utilize the range imaging depth sensor data in conjunction with the color image sensor to locate the X, Y, and Z coordinate positions of the left and right pupils using device specific mapping relationships associated with the range imaging depth camera and either an automated or a manual method to identify the X and Y pixel coordinates of the left and right pupils in the 2D color data (i.e., image).

By utilizing constant intrinsic parameters of the color image data to develop a pre-defined extrinsic linear relationship that defines the image scale as a function of the depth from sensor to object, the pupil distance calculator software is able to Compute the image scale using the extrinsic relationship and the averaged measured depth data (Z coordinate) to the left and right pupils. The pupil distance calculator software can then calculate the real world distance (e.g. millimeter or inch) between the center of the left and right pupils using the image scale and the distance between the left and right pupil centers in pixels.

Examples of range imaging depth cameras include, but are not limited to, RGB-D cameras such as the MICROSOFT KINECT. One of ordinary skill in the art would appreciate that there are numerous RGB-D cameras and other range imaging depth cameras that could be utilized with embodiments of the present invention, and embodiments of the present invention are contemplated for use with any appropriate RGB-D camera or other range imaging depth camera.

In another embodiment, the above method could replace the range imaging sensor with another sensor for determining depth (e.g., sonar). In these embodiments, the range imaging depth camera would comprise a depth determining means (e.g., sonar) and a color imaging sensor that captures 2D color data of the object within the color imaging sensor field of view. One of ordinary skill in the art would appreciate that there are numerous depth determining means that could be utilized with embodiments of the present invention, and embodiments of the present invention are contemplated for use with any appropriate depth determining means.

Figure 4:
FIG. 4 depicts the loaded image on a web portal in accordance with various embodiments of the present innovation.

In an embodiment of the present innovation, when the pupil distance is known, the image can be used to load to a web portal as shown in FIG. 4. The image is loaded on web-portal to try out different frames. The web portal contains frontal frame images that are sized to a constant scale, for example 2 pixels=1 mm. When the user image is loaded to the web portal, the subject image is resized to the same scale. In this case, the pupils are used as the scaling points. For example, if a user has a real life pupil distance of 60 mm, then the uploaded user image would be resized so that there are 120 pixels (60 mm I Constant Scale of 2) between the left and right eye X,Y coordinates. The user can try on different frames by superimposing the frame or sunglass on top of the subjects face. The resulting combined image is an accurate representation of the real life sizes.

The resulting combined image is an accurate representation of the real life sizes. This consistent scale allows the user to calculate the distance between any 2 points in the combined image. In addition to the interpupillary distance, other measurements are needed when manufacturing multi-focal lenses.

As presently known in the art, all lenses with additional elements in them such as bifocals, trifocals, and progressive lenses are considered multi-focal lenses. In These lenses may need a measurement known as the segment or "seg" height. The seg height is the distance from the bottom of the selected frame to the top of the multi-focal segment.

In an embodiment of the present innovation, eyeglass retailers and opticians make a determination where the seg height should be located based upon the location of the eyes in the frames (the combined image). Generally, bifocal lens elements are placed so that the seg height is at the lower lid of the eye; a tri-focal seg height would be at the bottom of the pupil. Progressive lenses have a seg height that is approximately the same as the vertical pupillary distance between the center of the pupil and the bottom of the frame.

The present innovation allows prescription eyewear retailers to determine the interpupillary and the seg height based upon an image imported by the user and the combined scaled images of the user and the frame.

In an embodiment of the present innovation, the fitting pad 102 is specifically not round in shape as the round object is more difficult to measure. In addition, the round object can only be 10-20 mm in width; the margin for error is very high. If the user selects points that are 1 mm in error, the resulting pupillary distance calculations can vary by 10% or more.

Although the present innovation has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except a combination where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

All documents referenced herein are hereby incorporated by reference.

The invention claimed is:

1. A method for measuring interpupillary distance, the method comprising the steps of:
   producing three dimensional spatial depth data from a range imaging sensor of a range imaging depth camera device to a person within a field of view of the range imaging sensor;
   capturing two dimensional color data of the object with a color imaging sensor of the range imaging depth camera device;

uploading said three dimensional spatial data and said two dimensional color data to a computing device;

mapping X, Y coordinates of the three dimensional spatial depth data with X, Y coordinates of the two dimensional color data through use of device specific mapping relationships between the range imaging depth sensor and the color imaging sensor; and utilizing the range imaging sensor to automatically locate X, Y, and Z coordinate positions of the left and right pupils of the person where the X and Y coordinate positions are centered on the pupil and the Z coordinate position is a distance from a plane located at the range imaging sensor to the surface of the left and right pupil.

2. The method of claim 1, further comprising the step of displaying said two dimensional color data in the form of an image on a display communicatively connected to said computing device.

3. The method of claim 2, wherein the computing device is further configured to provide indicators on the display that show estimated location points for the pupils of the person, wherein said estimated location points are based, at least in part, on said X, Y, and Z coordinate positions of the left and right pupils of the person.

4. The method of claim 3, wherein said computing device prompts the person to move the estimated location points for the pupils of the person.

5. The method of claim 1, wherein the computing device is configured with a touch screen display.

6. The method of claim 5, wherein the computing device receives signals relating to where the person touches the touchscreen and determines confirmation of the person with respect to the location of the pupils of the person in said two dimensional color data.

7. The method of claim 1, further comprising the step of presenting a virtual image of the person wearing a pair of glasses, wherein the glasses are sized in conjunction with said X, Y, and Z coordinate positions of the left and right pupils of the person.

8. A method for measuring interpupillary distance, the method comprising the steps of:

producing three dimensional spatial depth data from a range imaging sensor of a range imaging depth camera device to a person within a field of view of the range imaging sensor;

capturing two dimensional color data of the object with a color imaging sensor of the range imaging depth camera device;

uploading said three dimensional spatial data and said two dimensional color data to a computing device;

mapping X, Y coordinates of the three dimensional spatial depth data with X, Y coordinates of the two dimensional color data through use of device specific mapping relationships between the range imaging depth sensor and the color imaging sensor; and identifying X and Y pixel coordinate positions of a left and right pupil in the two dimensional color data, developing a pre-defined extrinsic linear relationship that defines image scale as a function of depth from the color imaging sensor to the person by using constant intrinsic parameters of the color imaging sensor;

computing image scale using the extrinsic linear relationship and the averaged measured depth data (Z coordinate) to the left and right pupils;

calculating a distance between centers of the left and right pupils using the image scale and number of pixels between the centers of the left and right pupil.

9. The method of claim 8, further comprising the step of displaying said two dimensional color data in the form of an image on a display communicatively connected to said computing device.

10. The method of claim 9, wherein the computing device is further configured to provide indicators on the display that show estimated location points for the pupils of the person, wherein said estimated location points are based, at least in part, on said X, Y, and Z coordinate positions of the left and right pupils of the person.

11. The method of claim 10, wherein said computing device prompts the person to move the estimated location points for the pupils of the person.

12. The method of claim 8, wherein the computing device is configured with a touch screen display.

13. The method of claim 12, wherein the computing device receives signals relating to where the person touches the touchscreen and determines confirmation of the person with respect to the location of the pupils of the person in said two dimensional color data.

14. The method of claim 8, further comprising the step of presenting a virtual image of the person wearing a pair of glasses, wherein the glasses are sized in conjunction with said X, Y, and Z coordinate positions of the left and right pupils of the person.

15. A range imaging depth system, comprising:

a range imaging sensor for producing three dimensional spatial depth data;

a color imaging sensor for capturing two dimensional color data; and a pupil distance calculator unit for incorporating device specific relationship information between the three dimensional spatial depth data and the two dimensional color data to map X,Y coordinates of the three dimensional spatial depth data with X,Y coordinates of the two dimensional color data.

16. The system of claim 15, further comprising a display communicatively connected to said pupil distance calculator unit, said display configured to display said two dimensional color data in the form of an image.

17. The system of claim 16, wherein the display provides indicators that show estimated location points for the pupils of the person, wherein said estimated location points are based, at least in part, on said X, Y, and Z coordinate positions of the left and right pupils of the person.

18. The system of claim 17, wherein said pupil distance calculator unit prompts the person, via the display, to move the estimated location points for the pupils of the person.

19. The system of claim 15, further comprising a touch screen display.

20. The system of claim 19, wherein the pupil distance calculator unit is configured to receive signals relating to where the person touches the touch screen display and determines confirmation of the person with respect to the location of the pupils of the person in said two dimensional color data.

* * * * *